(12) United States Patent
Owen

(10) Patent No.: US 7,536,898 B2
(45) Date of Patent: May 26, 2009

(54) QUANTITATIVE AEROSOL DILUTION SYSTEM

(75) Inventor: Miles C. Owen, Huntsville, AL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/859,124

(22) Filed: Sep. 21, 2007

(65) Prior Publication Data

US 2009/0044599 A1 Feb. 19, 2009

Related U.S. Application Data

(60) Provisional application No. 60/954,984, filed on Aug. 9, 2007.

(51) Int. Cl.
*G01N 1/00* (2006.01)
(52) U.S. Cl. .................................................. 73/28.04
(58) Field of Classification Search ............... 73/23.33, 73/24.03, 28.01, 28.04
See application file for complete search history.

(56) References Cited

U.S. PATENT DOCUMENTS

| | | | |
|---|---|---|---|
| 3,953,792 A | | 4/1976 | Fletcher et al. |
| 4,415,265 A | | 11/1983 | Campillo et al. |
| 4,836,032 A | * | 6/1989 | Redus et al. ............. 73/861.04 |
| 5,059,352 A | | 10/1991 | Carlon et al. |
| 5,203,201 A | * | 4/1993 | Gogins ........................... 73/38 |
| 5,537,879 A | * | 7/1996 | Malczewski et al. ...... 73/863.61 |
| 6,639,671 B1 | * | 10/2003 | Liu ............................. 356/336 |
| 7,430,893 B2 | * | 10/2008 | Grayfer et al. ............... 73/23.2 |
| 2007/0234777 A1 | * | 10/2007 | Damer et al. ................ 73/1.06 |

* cited by examiner

*Primary Examiner*—Hezron Williams
*Assistant Examiner*—Gunnar J Gissel
(74) *Attorney, Agent, or Firm*—Michael K. Gray

(57) ABSTRACT

An inlet conduit (32) connects to aerosol source (100) of an initial particle concentration. A first flow path having particle counter (62) connects to inlet conduit (32). A second flow path (36) connects to the inlet conduit (32) and branches to form third flow path (38) and fourth flow path (40) which meet at junction (50). A flow restrictor (42) is positioned in the third flow path (38). Filter (44) and a flow meter (46) are connected in the fourth flow path. An outlet path (52) connects to the junction (50). A low particle counter (54), a second filter (56) and a second flow meter (58) are positioned in the outlet path. The system can accurately perform a traceable measurement of the dilution factor of an aerosol particle concentration traceable to national standards and allows for traceable measurements of aerosol concentrations below the dynamic range of a given particle counter.

16 Claims, 3 Drawing Sheets

QUANTITATIVE AEROSOL DILUTION SYSTEM

PRIORITY CLAIMED

Benefit is claimed for provisional application No. 60/954,984 for "Quantitative Aerosol Dilution System" which was filed on Aug. 9, 2007.

DEDICATORY CLAUSE

The invention described herein may be manufactured, used and licensed by or for the U.S. Government for Governmental Purposes without payment of any royalties thereon.

BACKGROUND OF THE INVENTION

I. Field of the Invention

The present invention pertains generally to the field of aerosol metrology, and more particularly to an aerosol dilution device capable of providing traceable measurements of the dilution factor and hence aerosol concentrations that are lower or higher than the calibrated range of the particle counting device.

II. Discussion of the Background

The measurement of aerosol mass or number concentration is performed with particle counting devices that measure aerosol concentration over a finite dynamic range. When particle counters measure aerosol concentrations above their operating range, the detectors can become saturated or exhibit undesirable nonlinear behavior. The drawback from these measurement devices arises from the fact that the need to accurately measure aerosol concentrations above the instrument's dynamic range is frequently encountered in practice.

To overcome this obstacle, dilution techniques were employed where the aerosol concentration was diluted by separating the flow path of an aerosol into a filtered path and a non-filtered path. In the filtered path, a filter absorbed the aerosol particles to create relatively pure air which was then mixed with the unfiltered aerosol to create a diluted mix.

The diluted mix was then channeled to a particle counter whereafter the data was extrapolated to arrive at a particle concentration. Furthermore, the magnitude of the dilution factor created by the diluter is not measured traceable to national standards thereby making it impossible to know the accuracy of the dilution.

An example of this prior art technique is demonstrated in FIG. 1. Undiluted aerosol arrives at inlet 10 where it is separated into a filtered path 12 and an unfiltered path represented by capillary tube 14. Capillary tube 14 extends through a felt washer 16. The filtered path 12 leads to HEPA filters 18 which remove the particles in the aerosol to create pure air. The pure air exits the filtered path in the proximity of mixing cone 20 where the pure air is mixed with the undiluted aerosol which has traveled through capillary tube 14. A pressure gauge 22 is situated so as to measure an aerosol path differential pressure and a pressure gauge 24 is situated so as to measure a total path differential pressure. A pressure adjustment mechanism 26 is provided in the filtered path 12 to adjust the pressure of the pure air as it leaves the filtered path. The mixture of pure air and aerosol travels through outlet 28 onward to a particle counter (not shown).

Even when the above technique is employed, the results cannot be considered to provide true traceable particle concentrations (at either low or high levels of concentration) because there is no measurement of the dilution factor by the diluter that is made traceable to national standards through such quantities as flow rate and/or aerosol concentrations.

The traceable calibration of aerosol number concentration has been done in the past by having an aerosol electrometer primary standard measure the electronic current on the airflow and using this data to arrive at a given aerosol concentration that is traceable to national standards through measurement of electronic current, flow rate and the elementary charge on an electron. The drawback from this technique stemmed from the fact that the electrometer was unable to provide accurate data when the aerosol concentration dropped below thousands of particles per cubic centimeter. In practice the need to perform accurate measurements traceable to national standards of aerosol concentrations less than ten particles per cubic centimeter arises, and hence a dilution system that provides quantitative measurements of the dilution factor is needed to measure lower aerosol concentrations that are traceable to national standards.

SUMMARY OF THE INVENTION

The present invention can accurately perform a traceable measurement of the aerosol dilution factor through the arrangement of piping and the specialized placement of two calibrated flow meters downstream of two high efficiency filters. The two flow meters are calibrated to national standards thereby allowing the traceable measurement of the dilution factor to be accurately measured traceable to national standards.

This traceable quantitative dilution system allows the calibration of aerosol particle number concentration at lower magnitudes than the primary standard aerosol electrometer calibrator. The traceable quantitative dilution system also allows for traceable measurements of aerosol concentration above the dynamic range of a given particle counter to be accurately made.

Two traceable flow meters are utilized to measure a dilution factor as a ratio of mass flow rates, one flow meter placed downstream of a high efficiency filter and the other meter placed downstream of both a high efficiency filter and the chosen particle counter. The dilution system flow rate is provided by either the particle counter or the aerosol source, and does not have to be a specific magnitude, because the flow meters provide a dilution factor for a range of flow rates.

An aerosol particle is defined as either a solid or liquid particle suspended in a gas, with characteristic lengths (diameters for spherical particles) between 5 nm and at least 10 μm. Optimal results are obtained by using a monodisperse aerosol with this system. The range of particle diameters recommended for the system is between 100-500 nm. A monodisperse aerosol can be generated by different aerosol sources, with an atomizer in series with an electrostatic classifier being a practical suggestion.

In the present invention, traceable calibrations of low aerosol concentration are achieved by comparing a high concentration aerosol, measured by a high range particle counter calibrated to national standards, to the same aerosol with a diluted concentration, measured by the uncalibrated low concentration particle counter. There are many different particle counters that can be used in this system, for example, a condensation particle counter, an optical particle counter, or a photometer. The traceable dilution system measures the dilution factor as a ratio of traceable flow rates with calibrated flow meters.

Mass flow meters such as a thermal flow meter or a laminar flow element are examples of flow meters that, when properly calibrated, can be used in this dilution system. A combination of the traceable measurements of the dilution factor and traceable high aerosol concentration provide traceability for the low concentration aerosol measurements.

In the present invention, traceable measurements of the dilution factor can also be made when diluting a high concentration aerosol that is above the dynamic range of a particle counter down to a concentration that is within the range of the particle counter. The traceable measurement of the dilution factor enables accurate calculation of the high concentration aerosol that is above the dynamic range of the particle counter.

DESCRIPTION OF THE DRAWINGS

A more complete appreciation of the invention and many of the attendant advantages thereof will be readily obtained as the same becomes better understood by reference to the following detailed description when considered in connection with the accompanying drawings.

DETAILED DESCRIPTION

Figure 1:
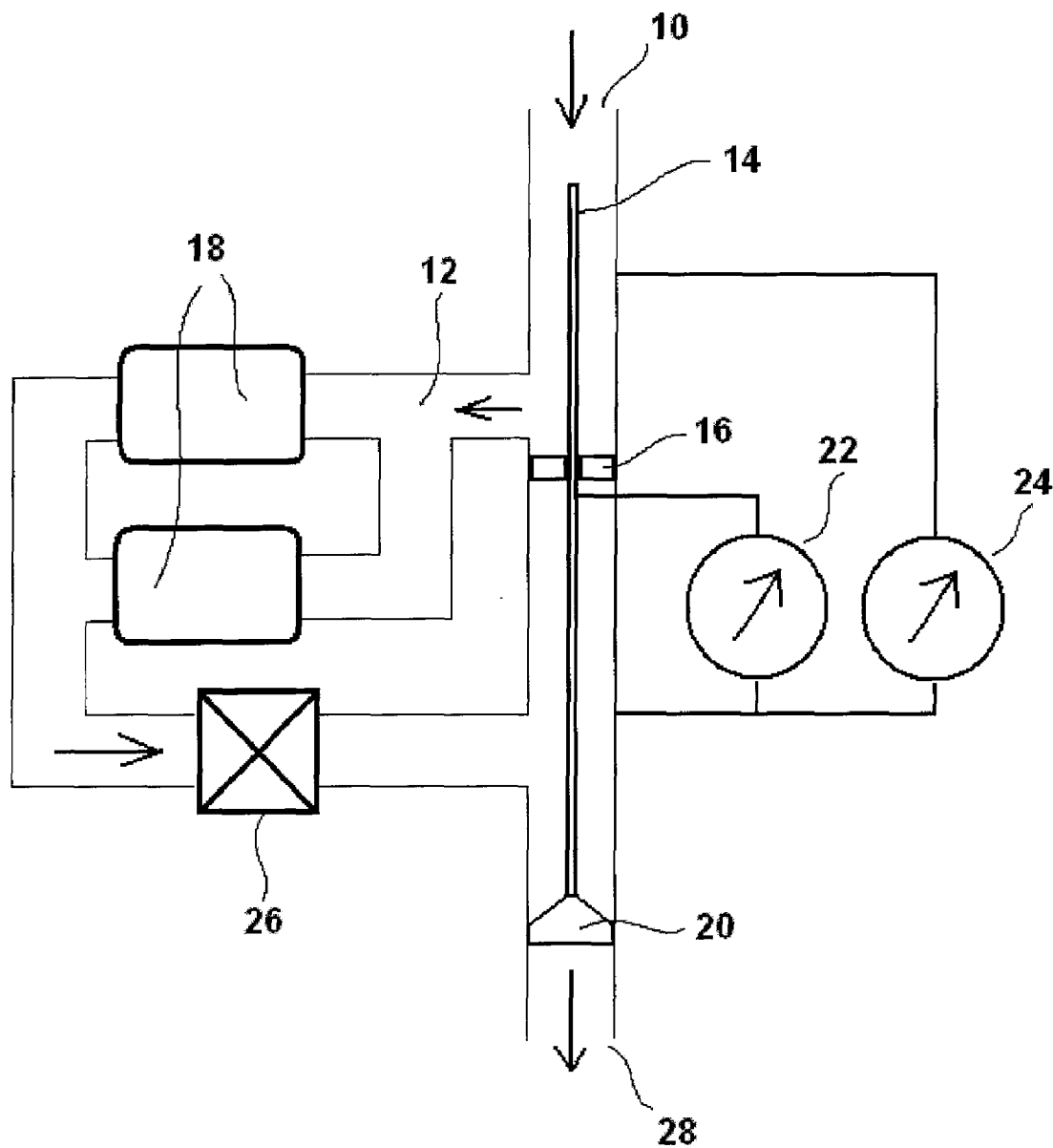
FIG. 1 is a prior art schematic illustration of an aerosol dilution system.
Figure 2:
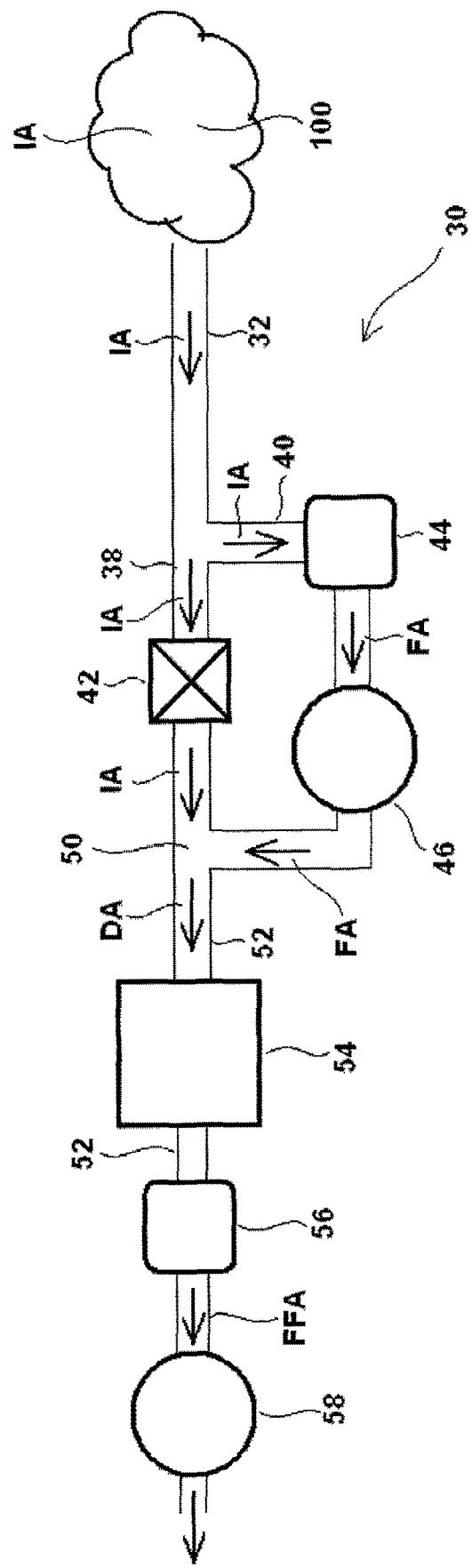
FIG. 2 is a schematic illustration of the quantitative aerosol dilution system of the present invention.

With reference to FIG. 2 of the drawings, the quantitative aerosol dilution system of the present invention has an inlet conduit 32 which originates at an aerosol source 100 where the aerosol has an input undiluted concentration of IA. Inlet conduit 32 branches into a flow path 38 and a flow path 40. A flow restrictor 42 regulates flow through flow path 38. Flow restrictor 42 can be various types of valves, such as pinch valves or metering valves, as well as different sized orifices or other such hardware designed to restrict fluid flow. It is recommended that a flow restrictor be used that restricts the flow by avoiding abrupt changes in flow path geometry, i.e., a flow restrictor that changes the flow path geometry in a streamlined fashion so that particle loss is minimized in the flow restrictor 42. A pinch valve is the practical recommendation. The flow restrictor is used to control the magnitude of the non-filtered flow rate.

The flow path 40 connects to a high efficiency filter 44 such as a HEPA filter or other filter designed to extract aerosol particles. The aerosol fluid traveling through the flow path 40 which flows through high efficiency filter 44 flows at a filtered flow rate to a dilution flow meter 46.

As a result of the filter 44, the particles in the aerosol traveling through the flow path 40 are filtered out so that the aerosol exiting the filter 44 is a filtered aerosol FA which in essence is pure air free of aerosol particles.

The filtered aerosol or air FA from the fluid path 40 and the undiluted aerosol of initial aerosol concentration IA from the fluid path 38 are combined at junction 50 so that a diluted aerosol concentration DA is created. The diluted aerosol concentration DA then continues on outlet path 52 to the particle counter 54, which in the prototype of the present invention was a condensation particle counter. The diluted aerosol concentration DA then travels to high efficiency filter 56 where the remaining aerosol particles are filtered out resulting in finally filtered air FFA being channeled along outlet path 52 to the dilution system flow meter 58. The arrangement of the HEPA filters 44 and 56, the flow meters 46 and 58, the particle counter 54, the flow restrictor 42, and the flow paths 32, 38, 40, 50 and 52 is what makes this system able to measure a traceable dilution factor.

In the configuration of FIG. 2, the aerosol source 100 can be considered to be above the calibrated range of particle counter 54. However, by measuring the dilution factor from the flow rate measurements of flow meters 46 and 58 and by utilizing the particle concentration from particle counter 54, an accurate traceable measurement of aerosol concentration IA from aerosol source 100 can be determined.

Figure 3:
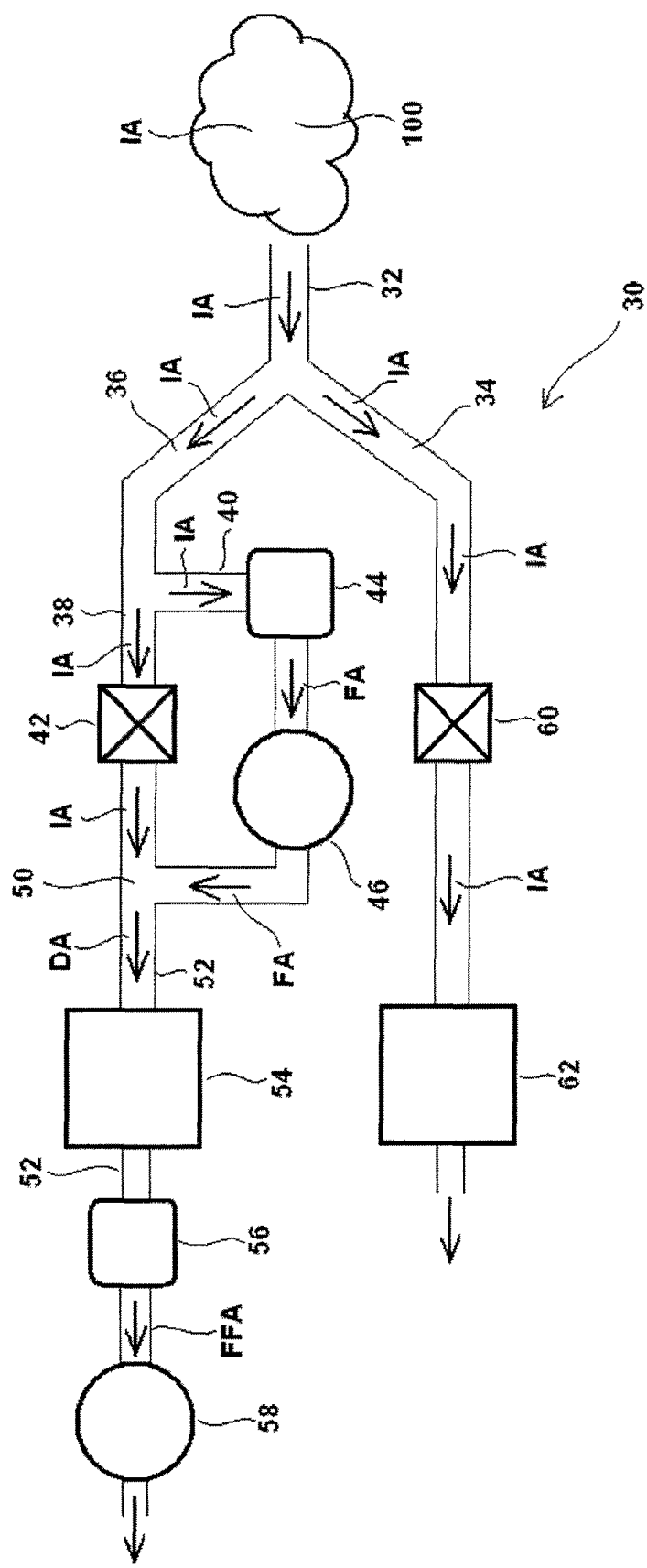
FIG. 3 is a schematic illustration of the quantitative aerosol dilution system of the present invention in an embodiment configured to measure aerosol concentrations below the traceable range of a calibrated particle counter.

With reference to FIG. 3, an embodiment of the quantitative aerosol dilution system of the present invention is configured to perform traceable measurements of aerosol concentrations below the magnitude of aerosol concentration that can be traceably measured with a calibrated particle counter.

The quantitative aerosol dilution system 30 (FIG. 3) has an inlet conduit 32 which originates at an aerosol source 100 where the aerosol has an input concentration of IA. Inlet conduit 32 branches into a first flow path 34 and a second flow path 36. The second flow path branches into a third flow path 38 and a fourth flow path 40. The third flow path 38 connects to a flow restrictor 42. Flow restrictor 42 can be various types of valves, such as pinch valves or metering valves, as well as different sized orifices or hardware designed to restrict fluid flow.

It is recommended that a flow restrictor be used that restricts the flow by avoiding abrupt changes in flow path geometry, ideally changing the flow path geometry in a streamlined fashion so that particle loss is minimized in the flow restrictor 42. A pinch valve is a practical recommendation. The flow restrictor is used to control the magnitude of the non-filtered flow rate.

The fourth flow path 40 connects to a high efficiency filter 44 such as a HEPA filter or other filter designed to extract aerosol particles. The aerosol traveling through the fourth flow path 40 which flows through the high efficiency filter 44 flows at a filtered flow rate to a dilution flow meter 46.

As a result of the filter 44, the particles in the aerosol traveling through the fourth flow path 40 have been filtered out so the aerosol exiting the filter is a filtered aerosol FA which in essence is pure air free of aerosol particles. The filtered aerosol or air FA from the fourth fluid path 40 and the undiluted aerosol of initial aerosol concentration IA from the third fluid flow path 38 are combined at junction 50 so that a diluted aerosol concentration DA is created.

This diluted aerosol concentration DA then continues on outlet path 52 to low concentration counter 54, which in the prototype of the present invention was a condensation particle counter. The diluted aerosol concentration DA then travels to high efficiency filter 56 where the remaining aerosol particles are filtered out resulting in finally filtered air FFA being channeled along outlet path 52 to the dilution system flow meter 58.

The initial aerosol concentration IA which travels through the first flow path 34 to the high concentration particle counter 62 travels through a conduit geometry which is similar to the conduit geometry of the third flow path 38 which connects to flow restrictor 42. In FIG. 3, the element represented by numeral 60 is an optional flow restrictor. If a valve is used as the flow restrictor 42 the same model valve should be installed and left completely open as flow restrictor 60, i.e., the third fluid flow path 38 and the first flow path 34 must have similar "twists and turns". It is noted that for certain flow restrictions with minimal bending or with streamlined bending an element 60 would not be necessary.

Furthermore, right angle bends in the flow paths containing the aerosol should be avoided—the flow paths should be as straight and as short as possible; however, the right angle bending at junction 50 is permissible because of the filtering of the aerosol along the fourth fluid path 40.

The length of the first flow path 34 from the inlet conduit 32 to the calibrated high concentration particle counter 62 should be generally equal to the combined length of the second flow path 36 plus the third flow path 38 plus the outlet flow path 52 to the dilution system flow meter. It is recommended that all flow paths be made of the same materials or combination of materials.

Traceability for low aerosol concentration is achieved through the traceable measurement of dilution system standard volumetric flow rates (mass flow rates) and the input (high) aerosol concentration. The mathematical description of the dilution factor and aerosol concentration equalities is presented below.

In the dilution system, the Q or flow rates of the input or initial non-filtered aerosol IA, and the filtered aerosol FA combine at junction 50. By using the conservation of mass, this relationship can be expressed as:

$$Q_{non\text{-}filtered} + Q_{filtered} = Q_{system} \tag{1}$$

Using equation one above, the measured dilution factor is defined as:

$$D = \frac{Q_{non\text{-}filtered}}{Q_{system}} = \frac{Q_{system} - Q_{filtered}}{Q_{system}} = 1 - \frac{Q_{filtered}}{Q_{system}} \tag{2}$$

The input aerosol concentration IA or $C_{input}$ is calculated by combining the diluted aerosol concentration DA or $C_{diluted}$ and the measured dilution factor of equation two as follows:

$$C_{input} = \frac{C_{diluted}}{D} \tag{3}$$

The result of equation three is then compared with the measured input aerosol concentration IA performed by the calibrated high concentration particle counter 62.

Finally, equation three is rearranged. The traceable input aerosol concentration IA or $C_{input}$ measured by the calibrated high concentration particle counter 62 is multiplied by the traceable dilution factor D of equation two. The result is the diluted aerosol concentration DA or $C_{diluted}$. This relationship is demonstrated in equation four below.

$$C_{input} D = C_{diluted} \tag{4}$$

Thus, traceable measurements of aerosol concentration can be determined at levels below that measured by a calibrated high concentration particle counter.

Traceability for high aerosol concentrations above the calibrated range of the particle counter is accomplished by utilizing flow rate information from flow meters 46 and 58 to arrive at the measured dilution factor D (equation two). When the dilution factor D is utilized with the diluted aerosol concentration measured by particle counter 54, traceable measurements of aerosol concentration at concentrations above the dynamic range of the particle counter can be realized.

In order to make accurate dilutions at low dilution factors as defined in equation two, special attention must be paid to the offset between the two flow meters 46 and 58. An offset between the two flow meters results in an aerosol concentration offset between the standard and unit under test particle counters as demonstrated in equation five below.

$$\begin{aligned} C_{diluted} &= C_{input} D \\ &= C_{input}\left[1 - \frac{(Q_{filtered} + q_{offset})}{Q_{system}}\right] \\ &= C_{input}\left(1 - \frac{Q_{filtered}}{Q_{system}}\right) - C_{input}\left(\frac{q_{offset}}{Q_{system}}\right) \end{aligned} \tag{5}$$

This offset between the two flow meters 46 and 58 designated in the above equation arises because two different flow meters, when measuring the same mass flow rate, generally give a different measured value of the same flow rate. This discrepancy is a result of the flow meter manufacturing and is very small for two similar flow meters. Nonetheless, this offset must be accounted for.

For convenience, the offset in equation five is designated as an additive flow rate to the filtered flow rate. At low concentrations this offset can dominate. To correct for this offset, all flow can be directed through both flow meters 46 and 58 by closing the flow restrictor 42. The two flow meters will then be measuring the same standard volumetric flow rate (mass flow rate), and any offset can be recorded and added to or subtracted from subsequent measurements of the two flow rates according to equation 5.

A supplemental method to correct for flow meter offset is applicable when the user has a calibration equation for both flow meters. This equation is generally a regression fit from the calibration of the flow meter used in the dilution system. In such a case, the offset between the two flow meters can be calculated from the calibration equations and incorporated into the measurements to obtain accurate results.

Finally, realizing accurate measurements of the unknown aerosol concentration from traceable measurements of the known aerosol concentration and the dilution factor also relies on the minimization of particle loss in the quantitative dilution system. For this reason a monodisperse aerosol within the previously mentioned particle diameter range is recommended. A flow restrictor with streamlined bending to create the restriction is also recommended, such as pinch valve.

If the flow restrictor 42 does not have streamlined bending, such as a metering valve or other hardware not exhibiting streamlined bending, it is recommended that the same model valve be installed as item 60 in FIG. 3 and left completely open in attempt to equalize particle loss in both flow paths and obtain accurate results.

Particle loss can further be minimized by optimizing the particle size for the dilution system geometry that corresponds to the minimum amount of particle loss. This optimization can be measured by using an electrostatic classifier and condensation particle counter in a scanning mobility particle sizing (SMPS) spectrometer configuration and measuring the monodisperse aerosol particle size that results in the least amount of particle loss through the dilution system. A practical suggestion for an SMPS spectrometer is available from TSI, Incorporated that utilizes a 3080 electrostatic classifier with a variety of condensation particle counter models. Furthermore, particle loss is minimized by avoiding abrupt changes in the flow geometry of the aforementioned respective flow paths.

To perform traceable measurements of low aerosol concentrations using this invention, the input aerosol concentration IA should be in the calibrated range of the calibrated high concentration particle counter 62. Any offset between the two flow meters 46 and 58 should be accounted for using one of the two aforementioned methods. Then, using the flow restrictor 42 to dilute the aerosol DA, the dilution factor is measured by particle counters 54 and 62. The measured values are combined using equation four to produce a traceable measurement of low aerosol concentration.

Conversely, for measuring higher aerosol concentrations that are out of the range of the particle counter, equation three is used to calculate $C_{input}$ to provide a traceable measurement of high aerosol concentration from traceable measurements of the dilution factor D and the diluted aerosol concentration $C_{diluted}$.

Through the arrangement of piping and the specialized placement of particle counters and two calibrated flow meters downstream of two high efficiency filters, the present invention can accurately perform a traceable measurement of a dilution factor and an aerosol particle concentration. The traceable quantitative dilution system of the present invention allows for the calibration of aerosol particle number concentrations at lower magnitudes than the primary standard aerosol electrometer calibrator and allows for traceable measurements of aerosol concentration above the dynamic range of a given particle counter to be accurately made.

Various modifications are possible without deviating from the spirit of the present invention. Accordingly, the scope of the invention is limited only by the claim language which follows hereafter.

What is claimed is:

1. An aerosol dilution system, comprising:
   an inlet conduit (32) connected to an aerosol source (100) having an initial particle concentration;
   a first flow path (34) connected to the inlet conduit (32), said first flow path having a high particle counter (62) positioned at an end thereof;
   a second flow path (36) connected to the inlet conduit (32), said second flow path branching to form a third flow path (38) and a fourth flow path (40), said third and said fourth flow paths meeting at a junction (50);
   a flow restrictor (42) positioned in said third flow path (38), the initial particle concentration of said aerosol source (100) and an initial particle concentration received by said flow restrictor being identical;
   a filter (44) and a flow meter (46) connected in series in said fourth flow path, said filter (44) being in direct contact with said aerosol source;
   an outlet path (52) connected to said junction (50), and wherein a low particle counter (54), a second filter (56) and a second flow meter (58) are positioned in said outlet path.

2. An aerosol dilution system according to claim 1, wherein:
   said first flow path is provided with a flow restrictor element (60) similar to said flow restrictor (42) located in said third flow path (38).

3. An aerosol dilution system according to claim 2, wherein:
   said flow restrictor element (60) is a valve.

4. An aerosol dilution system according to claim 1, wherein:
   said low particle counter (54) contained in said outlet path (52) counts the aerosol particles of a diluted aerosol concentration.

5. An aerosol dilution system according to claim 1, wherein:
   said high particle counter (62) counts the aerosol particles in an undiluted aerosol concentration which undiluted aerosol concentration is the same as the aerosol particle concentration contained in the aerosol source (100).

6. An aerosol dilution system according to claim 1, wherein:
   said flow meter (46) is positioned downstream of said filter (44) and said second flow meter (58) is positioned downstream of said second filter (56).

7. An aerosol dilution system according to claim 6, wherein:
   said flow meter (46) and said second flow meter (58) measure a dilution factor D expressed by:

$$D = \frac{Q_{non-filtered}}{Q_{system}} = \frac{Q_{system} - Q_{filtered}}{Q_{system}} = 1 - \frac{Q_{filtered}}{Q_{system}} \quad (2)$$

where $Q_{non-filtered}$ is equal to the mass flow rate measured by the said second flow meter (58) and $Q_{filtered}$ is equal to the mass flow rate measured by said flow meter (46) and where $$Q_{non-filtered} + Q_{filtered} = Q_{system} \quad (1)$$

8. An aerosol dilution system according to claim 7, wherein:
   said flow meter (46) and said second flow meter (58) are calibrated to national standards to allow for traceable measurement of the dilution factor to be accurately measured and made traceable to national standards.

9. An aerosol dilution system according to claim 7, wherein:
   the diluted aerosol concentration $C_{diluted}$ can be calculated by the following equation:

$$C_{input} D = C_{diluted} \quad (4)$$

where $C_{diluted}$ is the aerosol concentration detected by said particle counter (54).

10. An aerosol dilution system, comprising:
    an aerosol source (100);
    a filtered aerosol flow path (40) connected to said aerosol source;
    a first filter (44) and a dilution flow meter (46) located in said filtered aerosol flow path;
    an undiluted aerosol flow path (38) connected to said aerosol source;
    a junction (50) where said filtered aerosol flow path (40) and said undiluted aerosol flow path (38) meet and where a diluted aerosol concentration (DA) is formed;
    an outlet flow path (52) having a particle counter (54) for counting aerosol particles in said diluted aerosol concentration (DA);
    a second filter (56) located in said outlet flow path for removing the aerosol particles in said diluted aerosol concentration such that finally filtered air (FFA) exits said second filter;
    a flow meter (58) which receives said finally filtered air from said second filter; and
    a flow restrictor (42) located in said undiluted aerosol flow path (38).

11. A system according to claim 10, wherein:
    said flow restrictor (42) receives an undiluted concentration of aerosol from said aerosol source.

12. A system according to claim 10, wherein:
    said dilution flow meter (46) and said flow meter (58) measure a dilution factor D expressed by:

$$D = \frac{Q_{non-filtered}}{Q_{system}} = \frac{Q_{system} - Q_{filtered}}{Q_{system}} = 1 - \frac{Q_{filtered}}{Q_{system}} \quad (2)$$

where $Q_{non-filtered}$ is equal to the mass flow rate measured by the said flow meter (58) and $Q_{filtered}$ is equal to the mass flow rate measured by said dilution flow meter (46) and where $$Q_{non-filtered} + Q_{filtered} = Q_{system} \quad (1)$$

13. A system according to claim 10, wherein:
said first filter (44) and said second filter (56) are high efficiency filters.

14. An aerosol dilution system, comprising:
an aerosol source (100) having an initial particle concentration;
a first flow path (34) connected to the aerosol source, said first flow path having a particle counter (62) positioned at an end thereof;
a second flow path (36) connected to the aerosol source, said second flow path branching to form a third flow path (38) and a fourth flow path (40), said third and said fourth flow paths meeting at a junction (50);
a filter (44) and a flow meter (46) connected in series in said fourth flow path;
an outlet path (52) connected to said junction (50), and wherein a low particle counter (54), a second filter (56) and a second flow meter (58) are positioned in said outlet path;
a flow restrictor (42) positioned in said third flow path (38) and wherein said first flow path is provided with a flow restrictor element (60) similar to said flow restrictor (42) located in said third flow path.

15. A system according to claim 14, wherein:
said flow restrictor element (60) is a valve.

16. A system according to claim 14, wherein:
said flow meter (46) and said second flow meter (58) measure a dilution factor D expressed by:

$$D = \frac{Q_{non-filtered}}{Q_{system}} = \frac{Q_{system} - Q_{filtered}}{Q_{system}} = 1 - \frac{Q_{filtered}}{Q_{system}} \quad (2)$$

where $Q_{system}$ is equal to the mass flow rate measured by the said second flow meter (58) and $Q_{filtered}$ is equal to the mass flow rate measured by said flow meter (46) and where $$Q_{non-filtered} + Q_{filtered} = Q_{system} \quad (1)$$

* * * * *